(12) United States Patent
Khunt et al.

(10) Patent No.: US 8,288,592 B2
(45) Date of Patent: Oct. 16, 2012

(54) SOLID STATE FORMS OF TAPENTADOL SALTS

(75) Inventors: Mayur Devjibhai Khunt, Gujarat (IN); Sandipan Prabhurao Bondge, Maharashtra (IN); Vikas Daulatrao Ahirao, Maharashtra (IN); Depashri Vikas Ahirao, legal representative, Maharashtra (IN); Nitin Sharadchandra Pradhan, Maharashtra (IN)

(73) Assignee: Actavis Group PTC EHF (IS)

( * ) Notice: Subject to any disclaimer, the term of this patent is extended or adjusted under 35 U.S.C. 154(b) by 0 days.

(21) Appl. No.: 12/886,680

(22) Filed: Sep. 21, 2010

(65) Prior Publication Data

US 2011/0071120 A1    Mar. 24, 2011

(30) Foreign Application Priority Data

Sep. 22, 2009 (IN) .................. 2287/CHE/2009

(51) Int. Cl.
*C07C 211/00* (2006.01)
*A01N 37/36* (2006.01)

(52) U.S. Cl. .................. 564/374; 514/166

(58) Field of Classification Search .................. None
See application file for complete search history.

(56) References Cited

U.S. PATENT DOCUMENTS

| | | | |
|---|---|---|---|
| RE28,593 E | 10/1975 | Bethell et al. | |
| 4,252,951 A * | 2/1981 | Jackson et al. | 540/220 |
| 6,248,737 B1 | 6/2001 | Buschmann et al. | |
| 6,344,558 B1 | 2/2002 | Buschmann et al. | |
| 7,417,170 B2 | 8/2008 | Hell et al. | |
| 2006/0167318 A1 | 7/2006 | Jagusch et al. | |
| 2007/0213405 A1 | 9/2007 | Fischer et al. | |
| 2009/0149534 A1 | 6/2009 | Gruss | |
| 2009/0326271 A1 * | 12/2009 | Hell | 564/344 |

FOREIGN PATENT DOCUMENTS

| | | |
|---|---|---|
| EP | 0693475 B1 | 2/1998 |
| WO | 2004108658 A1 | 12/2004 |
| WO | 2005000788 A1 | 1/2005 |
| WO | 2008012046 A1 | 1/2008 |
| WO | 2008012047 A1 | 1/2008 |
| WO | 2008012283 A1 | 1/2008 |

OTHER PUBLICATIONS

Vippagunta et. al., Advanced Drug Del. Rev., 48, pp. 3-26, (2001).*
Braga et al., "Making crystals from crystals: a green route to crystal engineering and polymorphism" ChemComm 2005, 3635-3645.*
http://tuchem.en.made-in-china.com/product/AnJEDoayjQCm/China-Dibenzoyl-L-tartaric-Acid-Monohydrate-L-DBTA-H2O.html (2011).*

* cited by examiner

*Primary Examiner* — Susanna Moore
*Assistant Examiner* — Jennifer C Sawyer
(74) *Attorney, Agent, or Firm* — Cantor Colburn LLP

(57) ABSTRACT

Provided herein are novel solid state forms of tapentadol salts, process for their preparation, pharmaceutical compositions, and method of treating thereof. The tapentadol salts include an L-(−)-camphorsulfonate salt, a dibenzoyl-(L)-tartrate salt, a dibenzoyl-(D)-tartrate salt, a malate salt, a maleate salt, or a salicylate salt.

5 Claims, 12 Drawing Sheets

SOLID STATE FORMS OF TAPENTADOL SALTS

CROSS REFERENCE TO RELATED APPLICATION

This application claims the benefit of priority to Indian provisional application No. 2287/CHE/2009, filed on Sep. 22, 2009, which is incorporated herein by reference in its entirety.

FIELD OF THE INVENTION

The present invention relates to novel solid state forms of tapentadol salts, a process for their preparation, pharmaceutical compositions, and methods of treating thereof.

BACKGROUND

U.S. Reissue Patent No. USRE39593 discloses a variety of 1-phenyl-3-dimethylaminopropane compounds, processes for their preparation, pharmaceutical compositions comprising the compounds, and method of use thereof. These compounds have the utility as analgesic active ingredients in pharmaceutical compositions. Among them, tapentadol hydrochloride, 3-[(1R,2R)-3-(dimethylamino)-1-ethyl-2-methylpropyl]phenol hydrochloride, is a centrally-acting analgesic with a unique dual mode of action as an agonist at the μ-opioid receptor and as a norepinephrine reuptake inhibitor. Tapentadol hydrochloride is represented by the following structural formula:

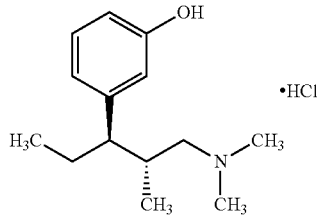

Various processes for the preparation of tapentadol, its enantiomers and related compounds, and their pharmaceutically acceptable salts are disclosed in U.S. Pat. Nos. 6,248,737 and 6,344,558; and PCT Publication Nos. WO 2004/108658, WO 2005/000788, WO 2008/012046, WO 2008/012047 and WO 2008/012283.

U.S. Pat. No. 6,248,737 (herein after referred to as the '737 patent) discloses processes for the preparation of tapentadol or a pharmaceutically acceptable salt thereof. While the '737 patent mentions that some of the disclosed compounds can form salts with physiologically acceptable acids, for example, hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid, only the hydrochloride salt had been prepared and isolated.

According to the '737 patent, tapentadol is prepared by the reaction of (−)-(2S,3S)-1-dimethylamino-3-(3-methoxyphenyl)-2-methylpentan-3-ol hydrochloride with thionyl chloride to produce (−)-(2S,3S)-[3-chloro-3-(3-methoxyphenyl)-2-methylpentyl]-dimethylamine hydrochloride, followed by subsequent removal of the 'Cl' substituent by treatment with zinc borohydride, zinc cyanoborohydride or tin cyanoborohydride, to produce (−)-(2R,3R)-[3-(3-methoxyphenyl)-2-methylpentyl]-dimethylamine hydrochloride. The (−)-(2R,3R)-[3-(3-methoxy phenyl)-2-methylpentyl]-dimethylamine hydrochloride is then converted to (−)-(1R,2R)-3-(3-dimethylamino-1-ethyl-2-methylpropyl)-phenol (tapentadol) by reacting with concentrated hydrobromic acid at reflux.

U.S. Patent Application No. 2007/0213405 (hereinafter referred to as the '405 application) discloses two crystalline polymorphs (Form A & Form B) of (−)-(1R,2R)-3-(3-dimethylamino-1-ethyl-2-methylpropyl)-phenol hydrochloride (tapentadol hydrochloride), and characterizes them by powder X-ray diffraction (P-XRD), Infra Red spectroscopy (IR), RAMAN spectroscopy and crystal structure analysis. The '405 application further teaches that the procedure described in example 25 of U.S. Pat. No. 6,248,737 and U.S. Pat. No. 6,344,558 as well as EP 693475 B1 produces crystalline Form B of tapentadol hydrochloride.

U.S. Patent Application No. 2009/0149534 (hereinafter referred to as the '534 application) discloses three crystalline modifications (modifications A, B & C) of tapentadol base, processes for their preparation, and characterizes the modifications by powder X-ray diffraction (P-XRD) pattern and RAMAN spectroscopy.

There remains a need for novel solid state forms of tapentadol salts.

SUMMARY

In one aspect, provided herein are novel solid state forms of a tapentadol salt, wherein the salt is an L-(−)-camphorsulfonate salt, a dibenzoyl-(L)-tartrate salt, a dibenzoyl-(D)-tartrate salt, a malate salt, a maleate salt or a salicylate salt.

In another aspect, tapentadol salts in a crystalline form are provided. In yet another aspect, tapentadol salts in an amorphous form are provided. In still another aspect, the solid state forms of tapentadol salts exist in an anhydrous and/or solvent-free form or as a hydrate and/or a solvate form.

In another aspect, encompassed herein is a process for preparing a solid state form of a tapentadol salt comprising contacting tapentadol free base with an acid in a suitable solvent under suitable conditions to produce a reaction mass, and isolating the solid state form of tapentadol acid addition salt, wherein the acid addition salt of tapentadol is an L-(−)-camphorsulfonate salt, a dibenzoyl-(L)-tartrate salt, a dibenzoyl-(D)-tartrate salt, a malate salt, a maleate salt or a salicylate salt.

In another aspect, provided herein is a method for treating a patient suffering from severe acute pain; comprising administering a solid state form of tapentadol salt, or a pharmaceutical composition that comprises the solid state form of tapentadol salt along with pharmaceutically acceptable excipients, wherein the salt of tapentadol is an L-(−)-camphorsulfonate salt, a dibenzoyl-(L)-tartrate salt, a dibenzoyl-(D)-tartrate salt, a malate salt, a maleate salt or a salicylate salt.

In another aspect, provided herein is a pharmaceutical composition comprising a solid state form of tapentadol salt as disclosed herein, and one or more pharmaceutically acceptable excipients.

In still another aspect, provided herein is a pharmaceutical composition comprising a solid state form of tapentadol salt made by the process disclosed herein, and one or more pharmaceutically acceptable excipients.

In still further aspect, encompassed herein is a process for preparing a pharmaceutical formulation comprising combining any one of the solid state forms of tapentadol salts disclosed herein with one or more pharmaceutically acceptable excipients.

In another aspect, the solid state forms of tapentadol salts disclosed herein for use in the pharmaceutical compositions have a $D_{90}$ particle size of less than or equal to about 500 microns, specifically about 1 micron to about 300 microns, and most specifically about 10 microns to about 150 microns.

DETAILED DESCRIPTION

Figure 1:
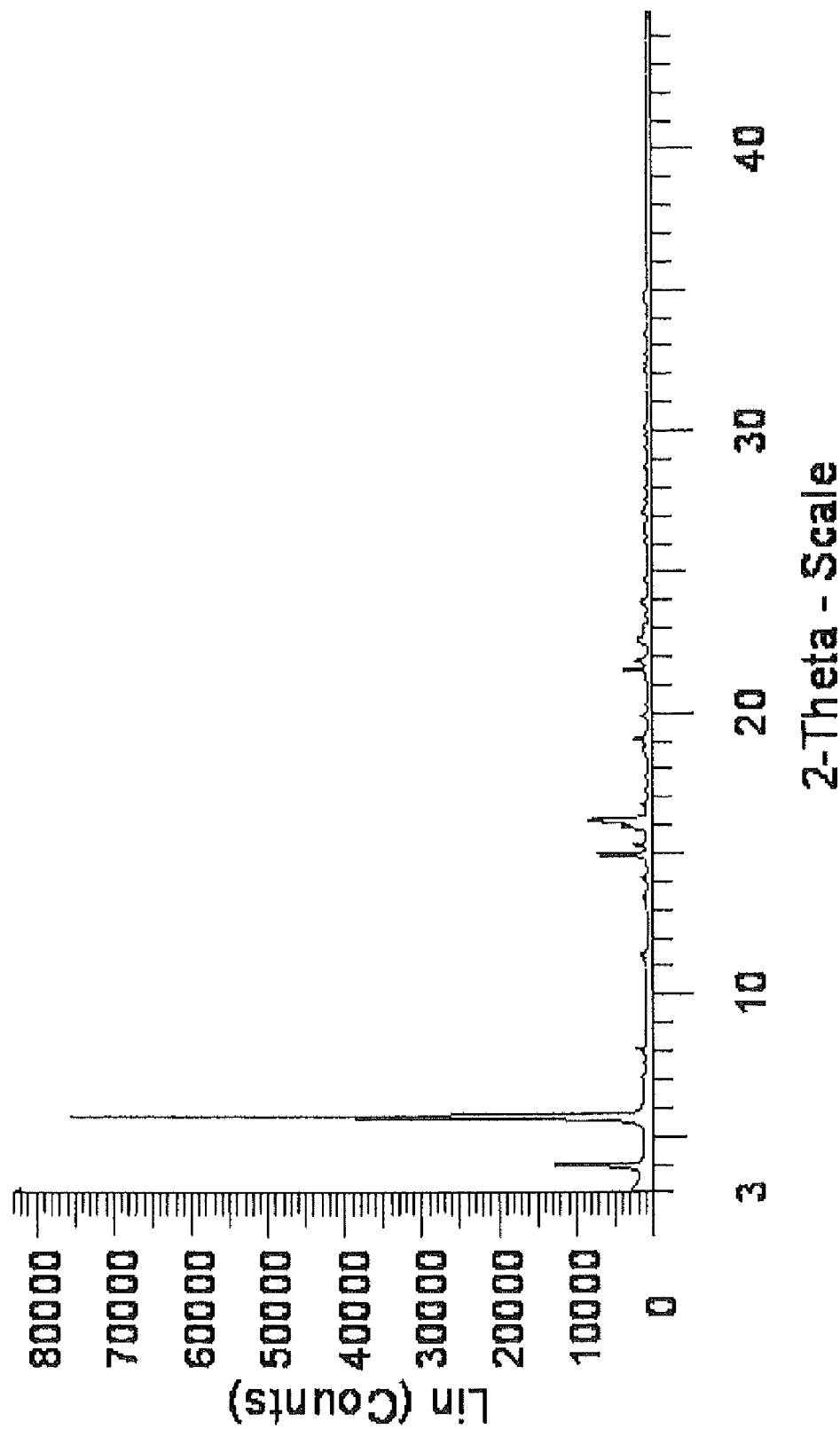
FIG. 1 is a characteristic Powder X-ray Diffraction (XRD) pattern of solid state form of tapentadol L-(−)-camphorsulfonate salt.

Solid state forms of tapentadol salts, except the hydrochloride salt, have not been reported, isolated, or characterized in the literature. The present inventors have surprisingly and unexpectedly found that some of the acid addition salts of 3-[(1R,2R)-3-(dimethylamino)-1-ethyl-2-methylpropyl]phenol, i.e., tapentadol salts, specifically, L-(−)-camphorsulfonate, dibenzoyl-(L)-tartrate salt, dibenzoyl-(D)-tartrate salt, malate, maleate and salicylate salts, can be isolated as solid state forms.

It has also been found that the solid state forms of tapentadol salts are useful intermediates in the preparation of tapentadol or a pharmaceutically acceptable salt thereof in high purity. The solid state forms of tapentadol salts have good flow properties, and are stable at room temperature, enhanced temperature, at relative high humidities, and in aqueous media. The novel solid state forms of tapentadol salts are suitable for formulating tapentadol.

In the formulation of drug compositions, it is important for the active pharmaceutical ingredient to be in a form in which it can be conveniently handled and processed. Convenient handling is important not only from the perspective of obtaining a commercially viable manufacturing process, but also from the perspective of subsequent manufacture of pharmaceutical formulations (e.g., oral dosage forms such as tablets) comprising the active pharmaceutical ingredient.

Chemical stability, solid state stability, and "shelf life" of the active pharmaceutical ingredient are important properties for a pharmaceutically active compound. The active pharmaceutical ingredient, and compositions containing it, should be capable of being effectively stored over appreciable periods of time, without exhibiting a significant change in the physico-chemical characteristics of the active pharmaceutical ingredient, e.g., its chemical composition, density, hygroscopicity and solubility. Thus, in the manufacture of commercially viable and pharmaceutically acceptable drug compositions, it is important, wherever possible, to provide the active pharmaceutical ingredient in a stable form.

New solid state forms of a pharmaceutical agent can further the development of formulations for the treatment of illnesses. For instance, solid forms of a compound are known in the pharmaceutical arts to affect, for example, the solubility, dissolution rate, bioavailability, chemical and physical stability, flowability, fractability, and compressibility of the compound, as well as the safety and efficacy of drug products based on the compound.

The discovery of novel salts in solid state form of pharmaceutically useful compounds provides a new opportunity to improve the performance characteristics of a pharmaceutical product. It also adds value to the material that a formulation scientist can use the same for designing, for example, a pharmaceutical dosage form of a drug with a targeted release profile or other desired characteristic.

According to one aspect, provided herein are novel and stable solid state forms of tapentadol salts, wherein the salt of tapentadol is an L-(−)-camphorsulfonate salt, a dibenzoyl-(L)-tartrate salt, a dibenzoyl-(D)-tartrate salt, a malate salt, a maleate salt or a salicylate salt.

In one embodiment, the solid state forms of tapentadol salts exist in a crystalline form. In another embodiment, the solid state forms of tapentadol salts exist in an amorphous form. In yet another embodiment, the solid state forms of tapentadol salts exist in an anhydrous and/or solvent-free form, or as a hydrate and/or a solvate form. Such solvated or hydrated forms may be present as hemi-, mono-, sesqui-, di- or tri-solvates or hydrates. Solvates and hydrates may be formed as a result of the solvents used during the formation of the tapentadol salts becoming embedded in the solid lattice structure. Because formation of the solvates and hydrates occurs during the preparation of tapentadol salts, formation of a particular solvated or hydrated form depends greatly on the conditions and method used to prepare the salt. Solvents should be pharmaceutically acceptable.

Figure 2:
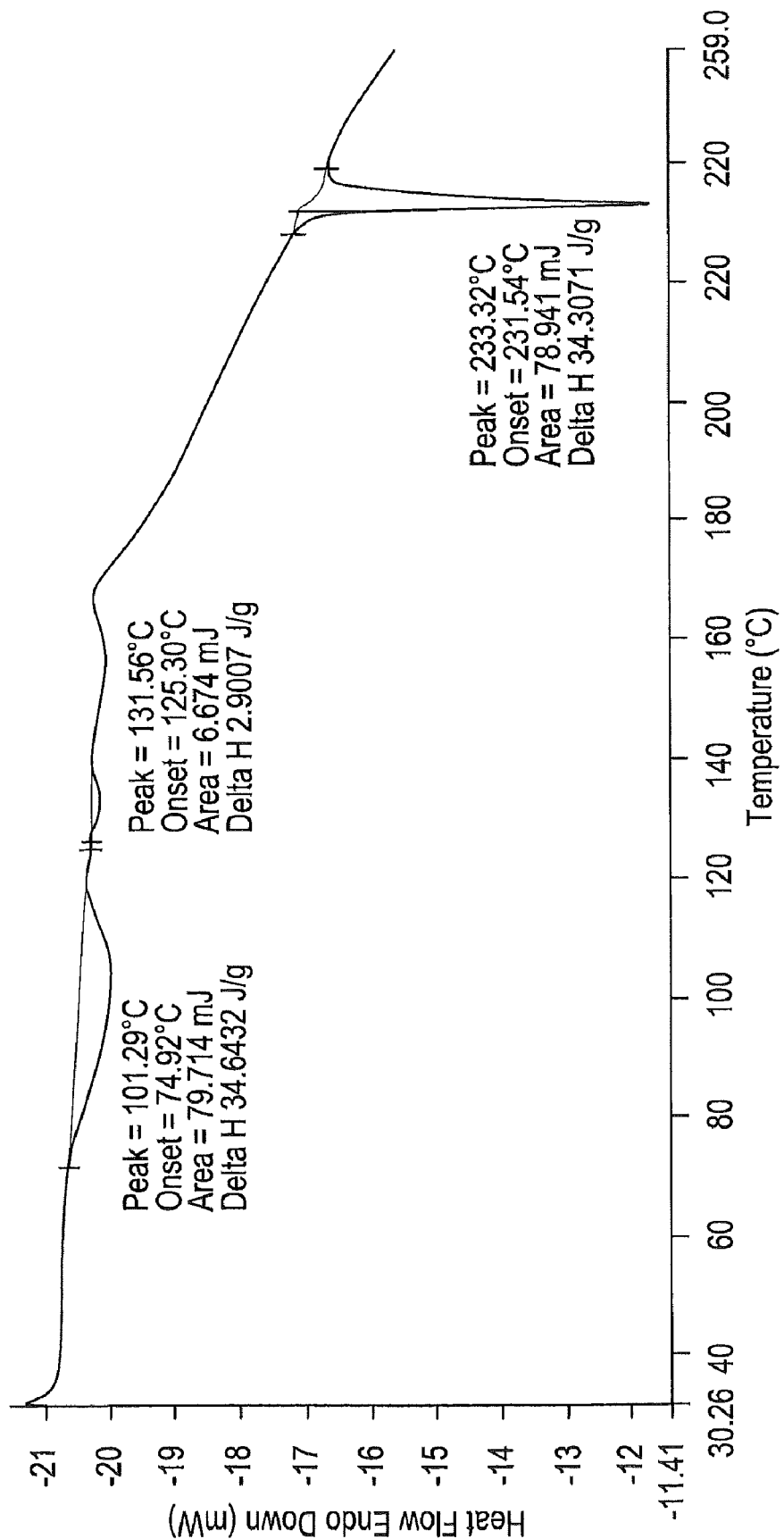
FIG. 2 is a characteristic Differential Scanning Calorimetric (DSC) thermogram of solid state form of tapentadol L-(−)-camphorsulfonate salt.
Figure 3:
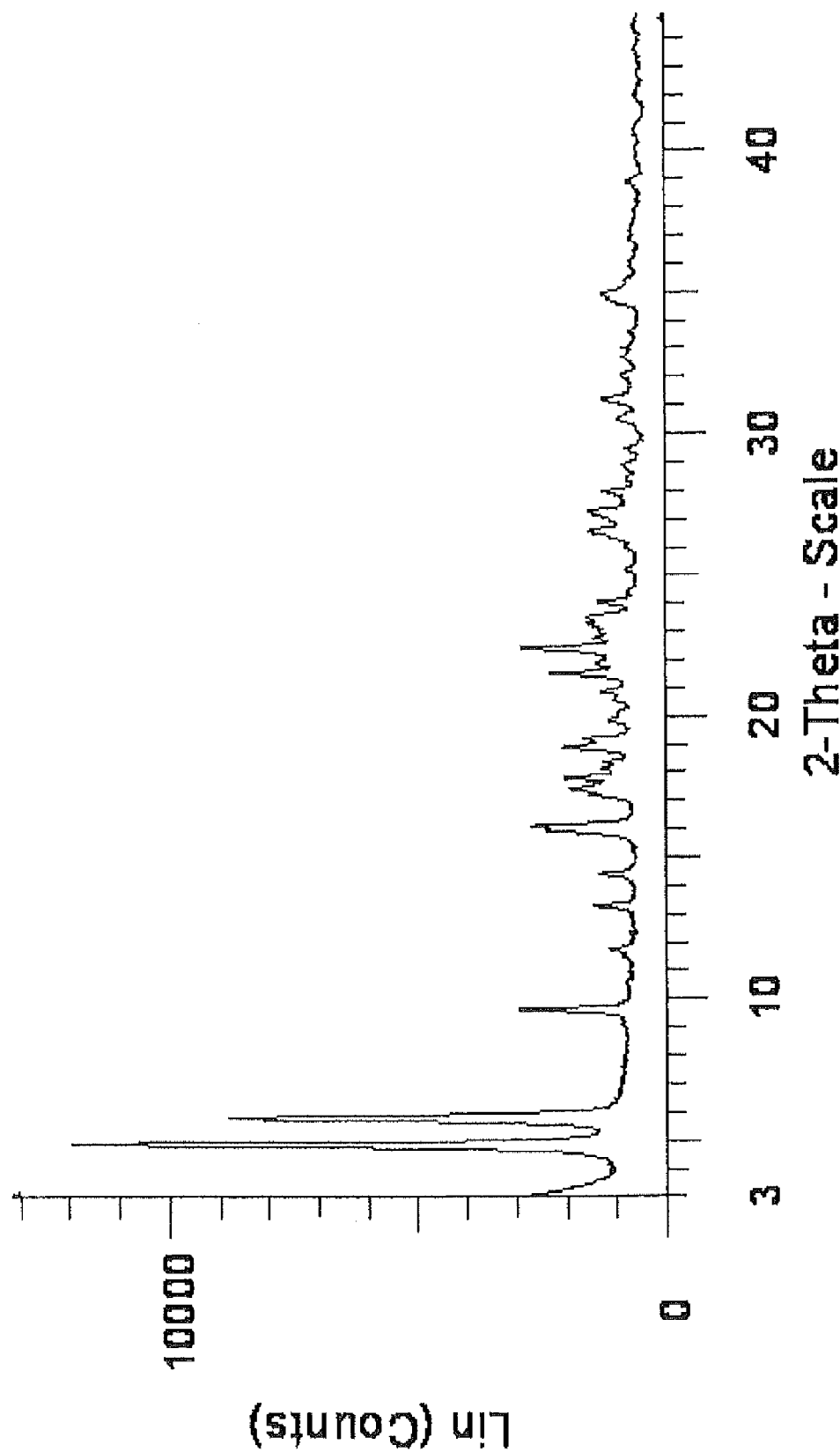
FIG. 3 is a characteristic Powder X-ray Diffraction (XRD) pattern of solid state form of tapentadol dibenzoyl-(L)-tartrate salt.
Figure 4:
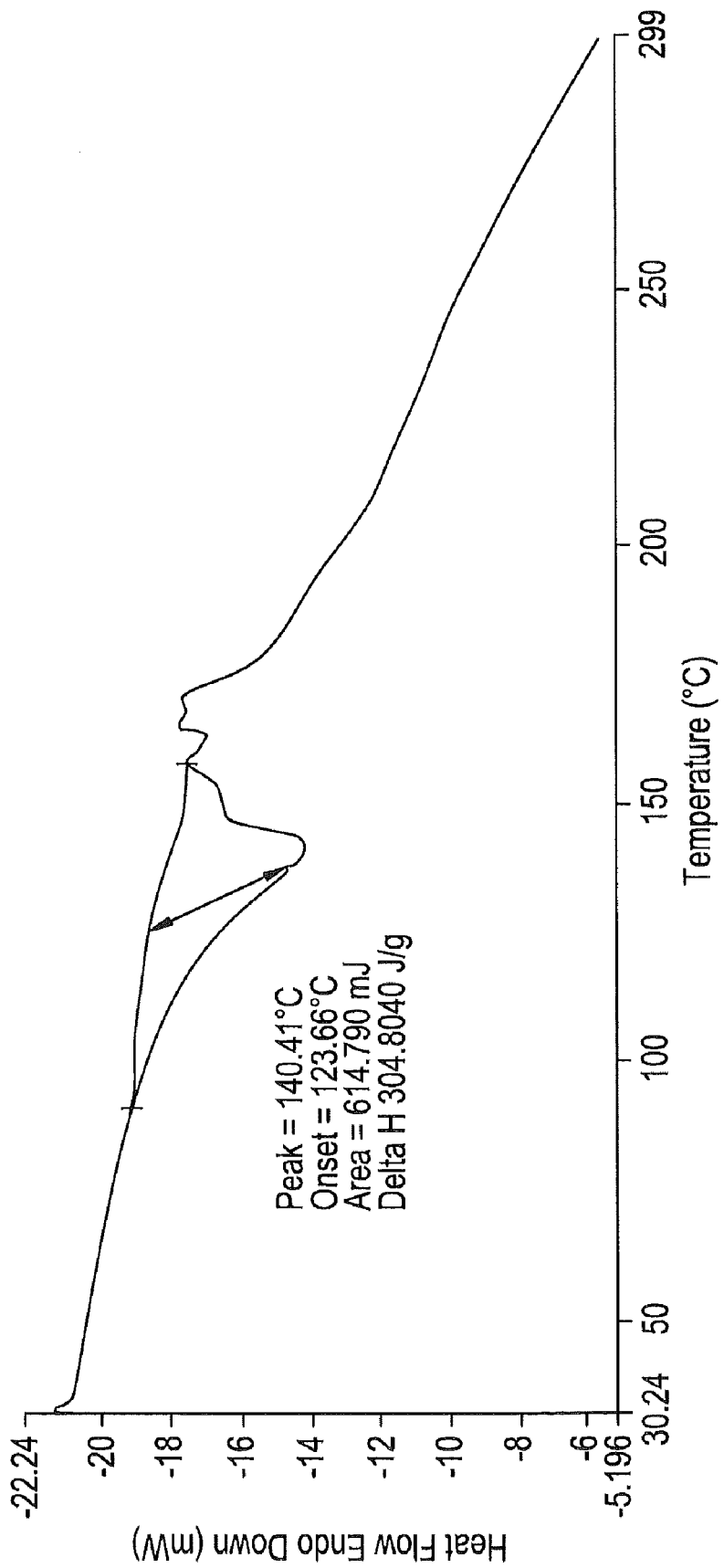
FIG. 4 is a characteristic Differential Scanning Calorimetric (DSC) thermogram of solid state form of tapentadol dibenzoyl-(L)-tartrate salt.
Figure 5:
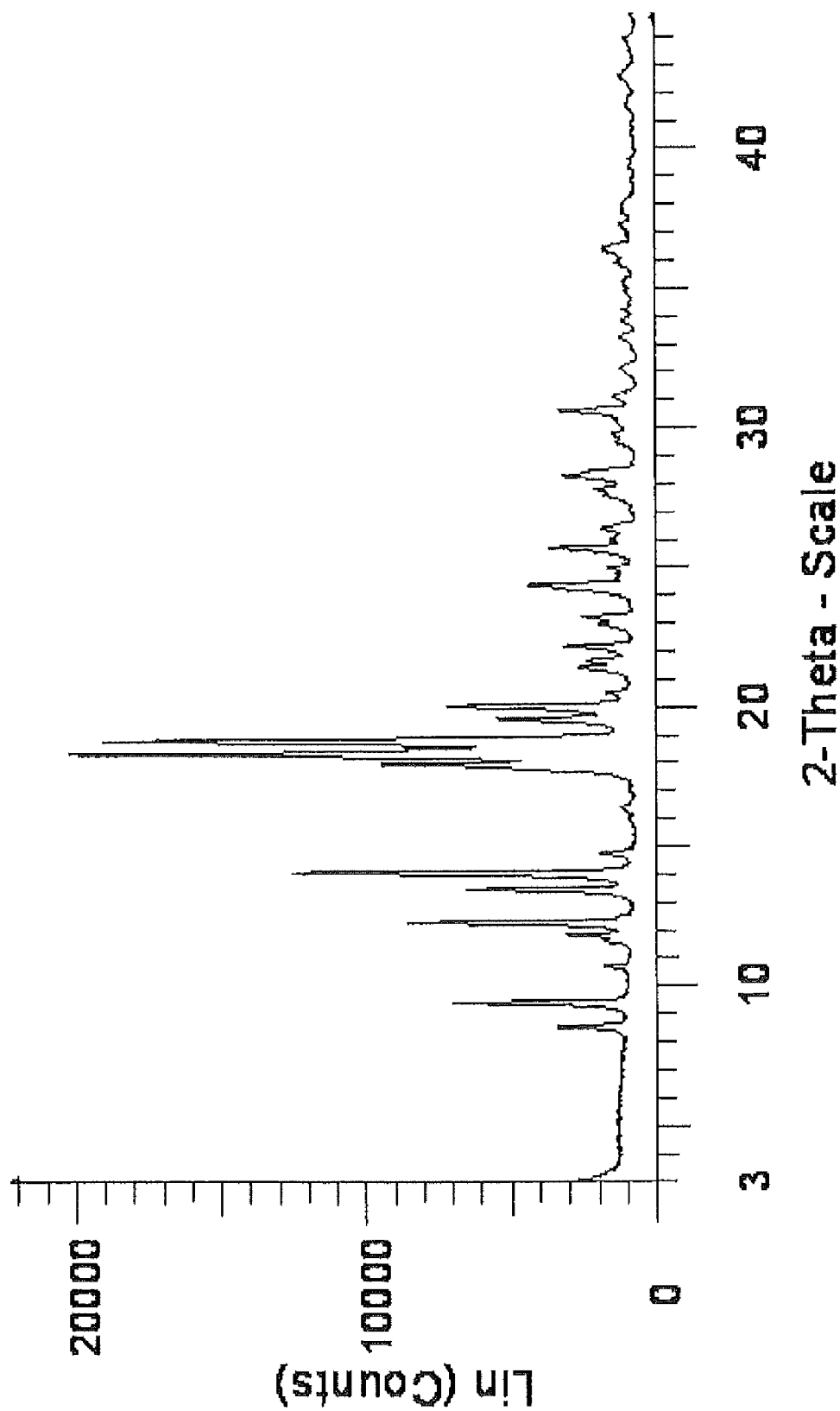
FIG. 5 is a characteristic Powder X-ray Diffraction (XRD) pattern of solid state form of tapentadol dibenzoyl-(D)-tartrate salt.
Figure 6:
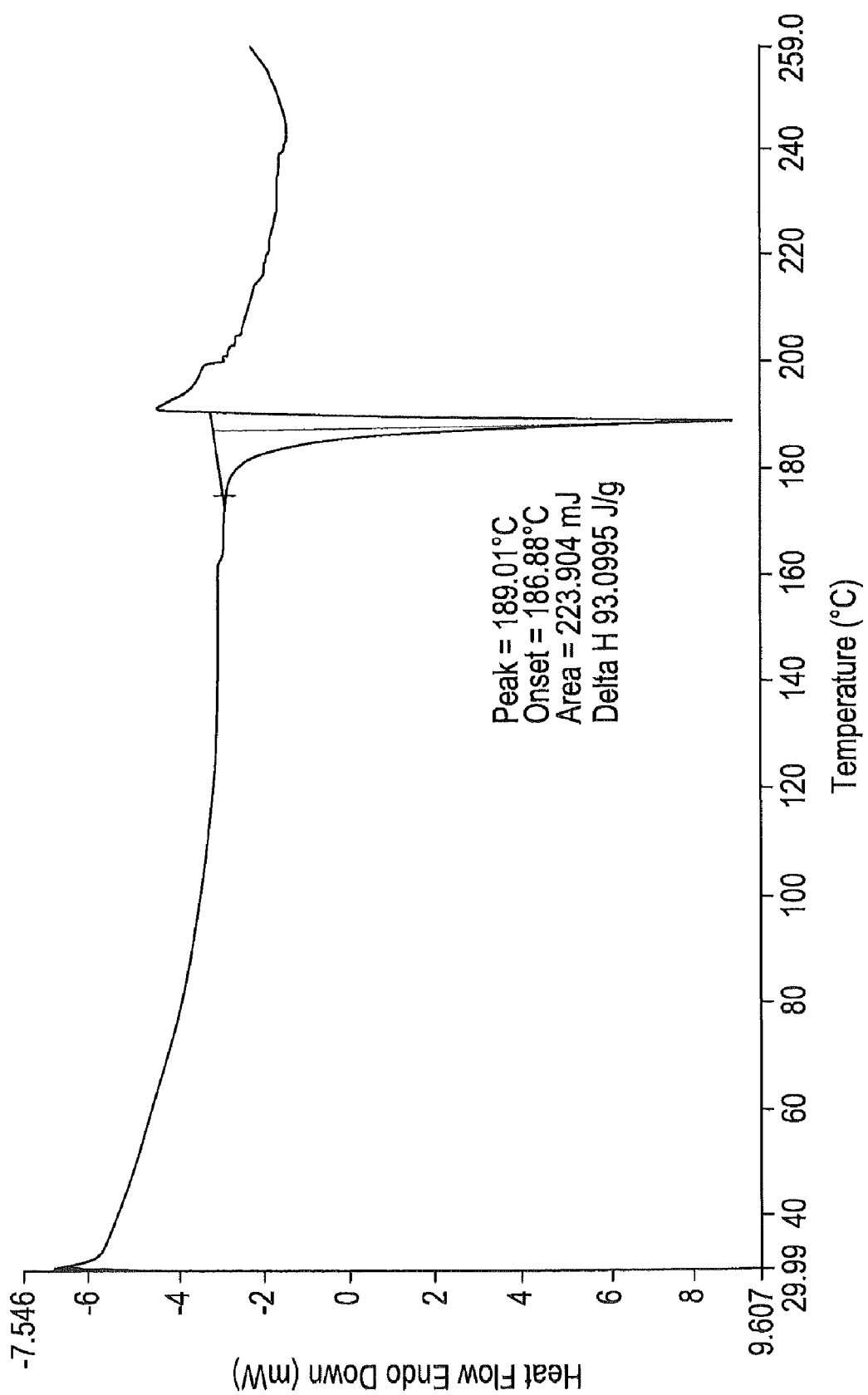
FIG. 6 is a characteristic Differential Scanning Calorimetric (DSC) thermogram of solid state form of tapentadol dibenzoyl-(D)-tartrate salt.
Figure 7:
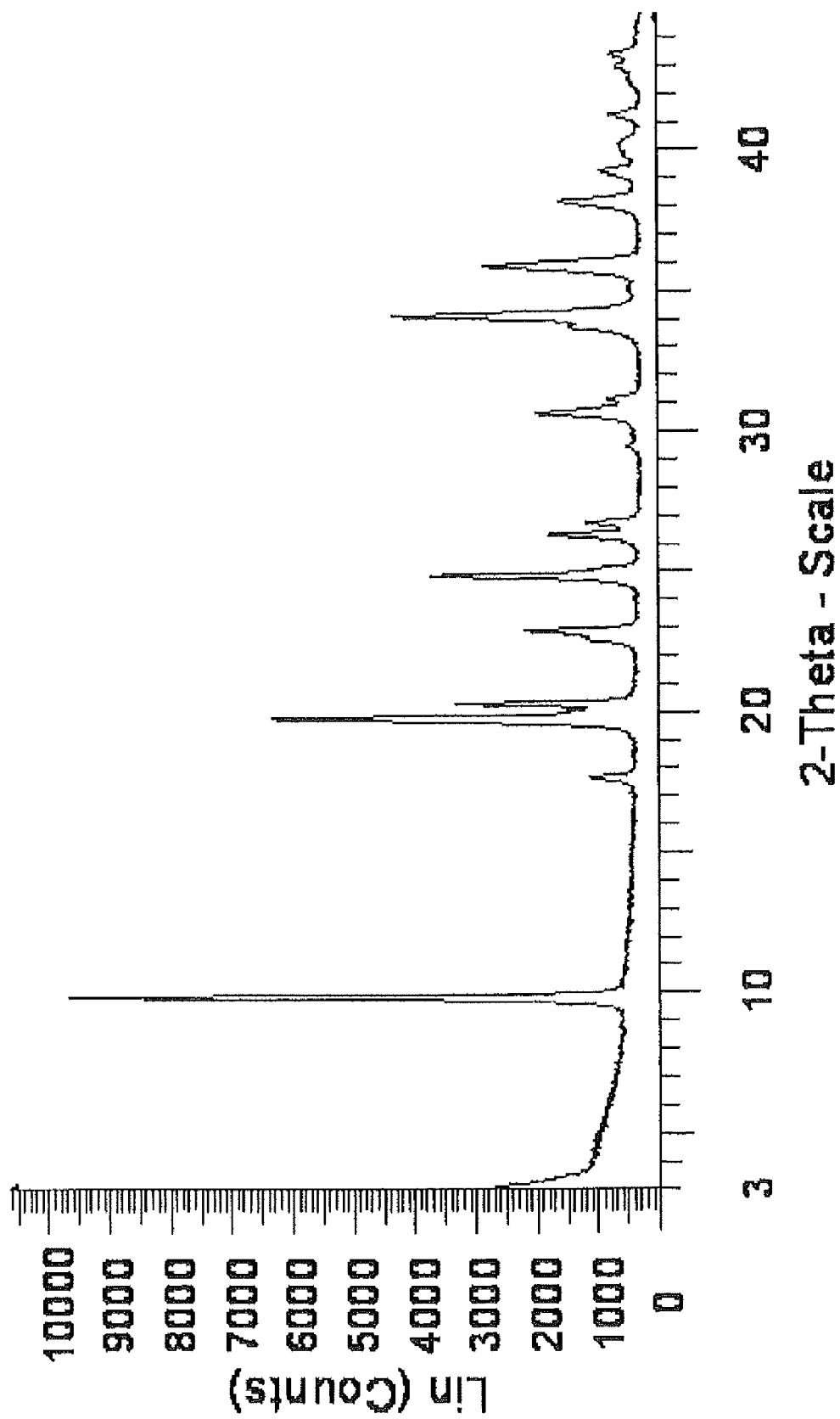
FIG. 7 is a characteristic Powder X-ray Diffraction (XRD) pattern of solid state form of tapentadol malate salt.
Figure 8:
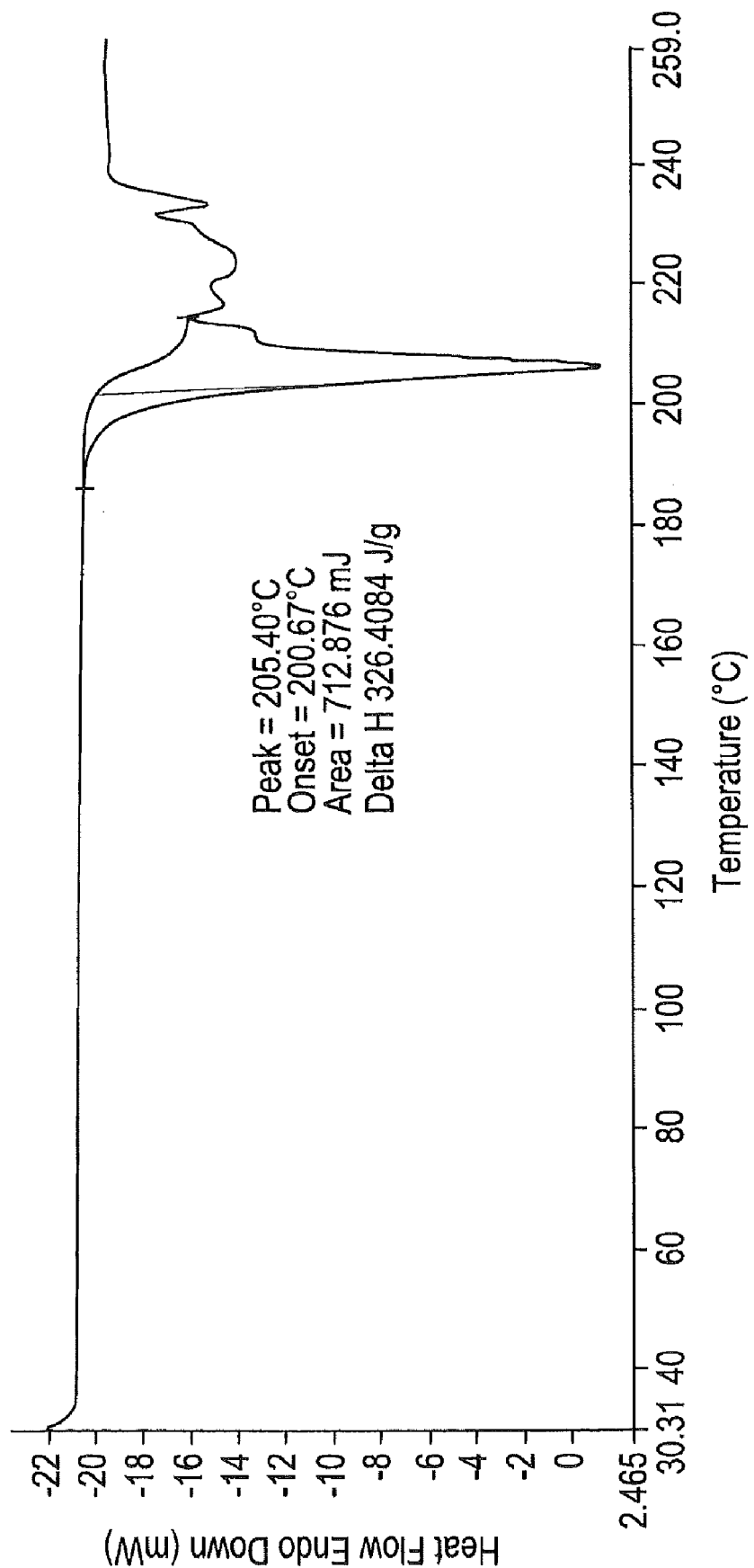
FIG. 8 is a characteristic Differential Scanning Calorimetric (DSC) thermogram of solid state form of tapentadol malate salt.
Figure 9:
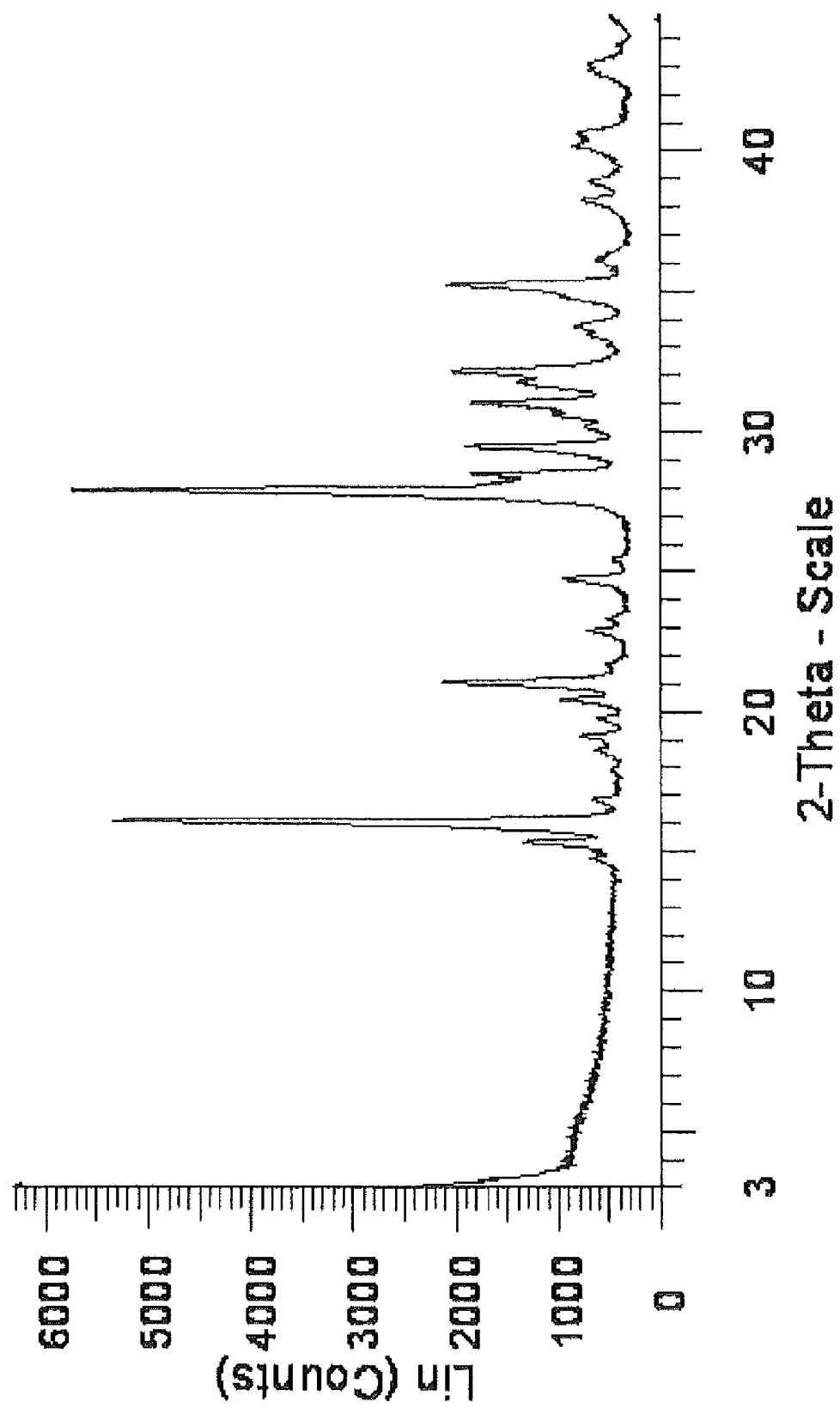
FIG. 9 is a characteristic Powder X-ray Diffraction (XRD) pattern of solid state form of tapentadol maleate salt.
Figure 10:
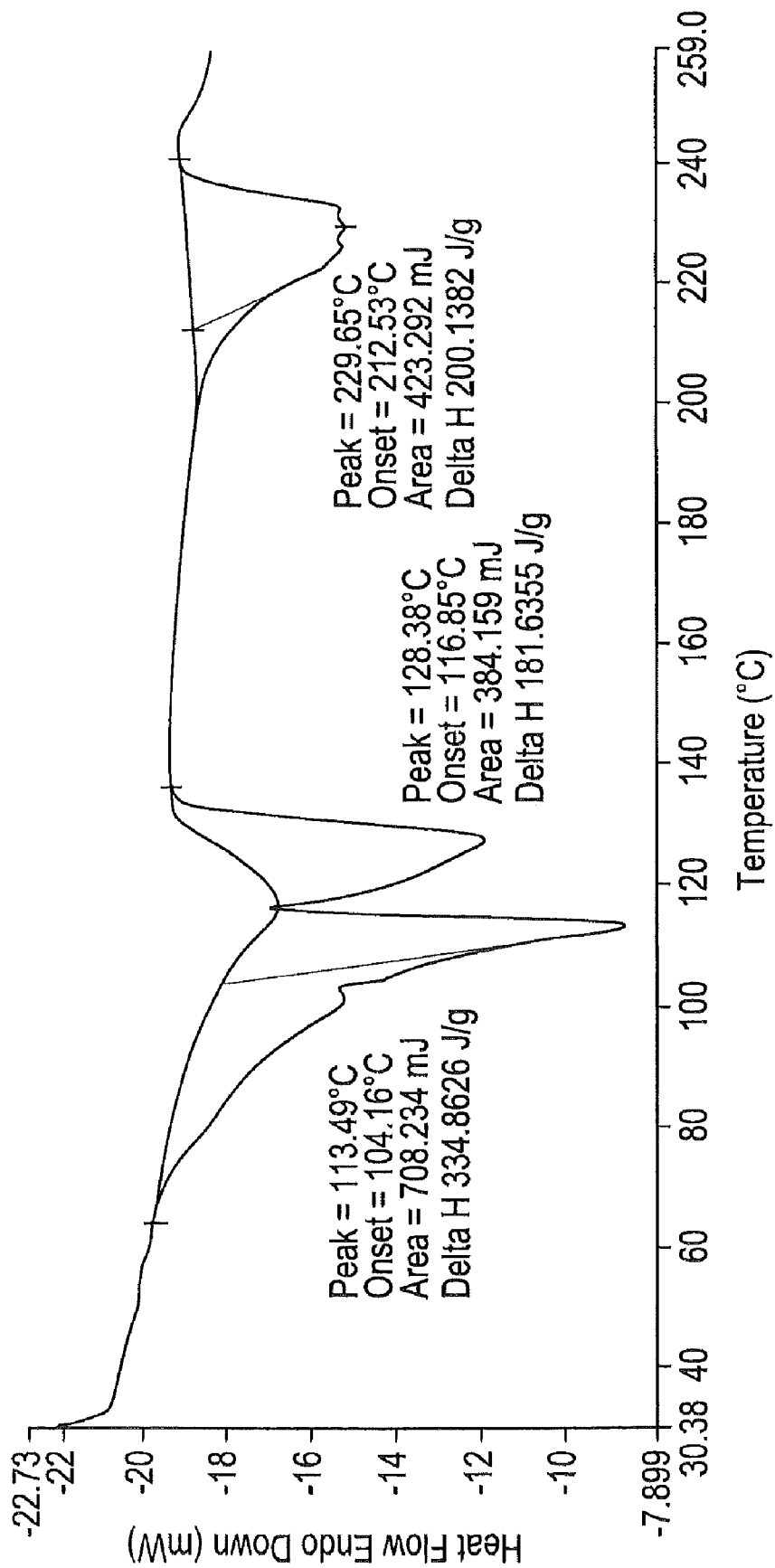
FIG. 10 is a characteristic Differential Scanning Calorimetric (DSC) thermogram of solid state form of tapentadol maleate salt.
Figure 11:
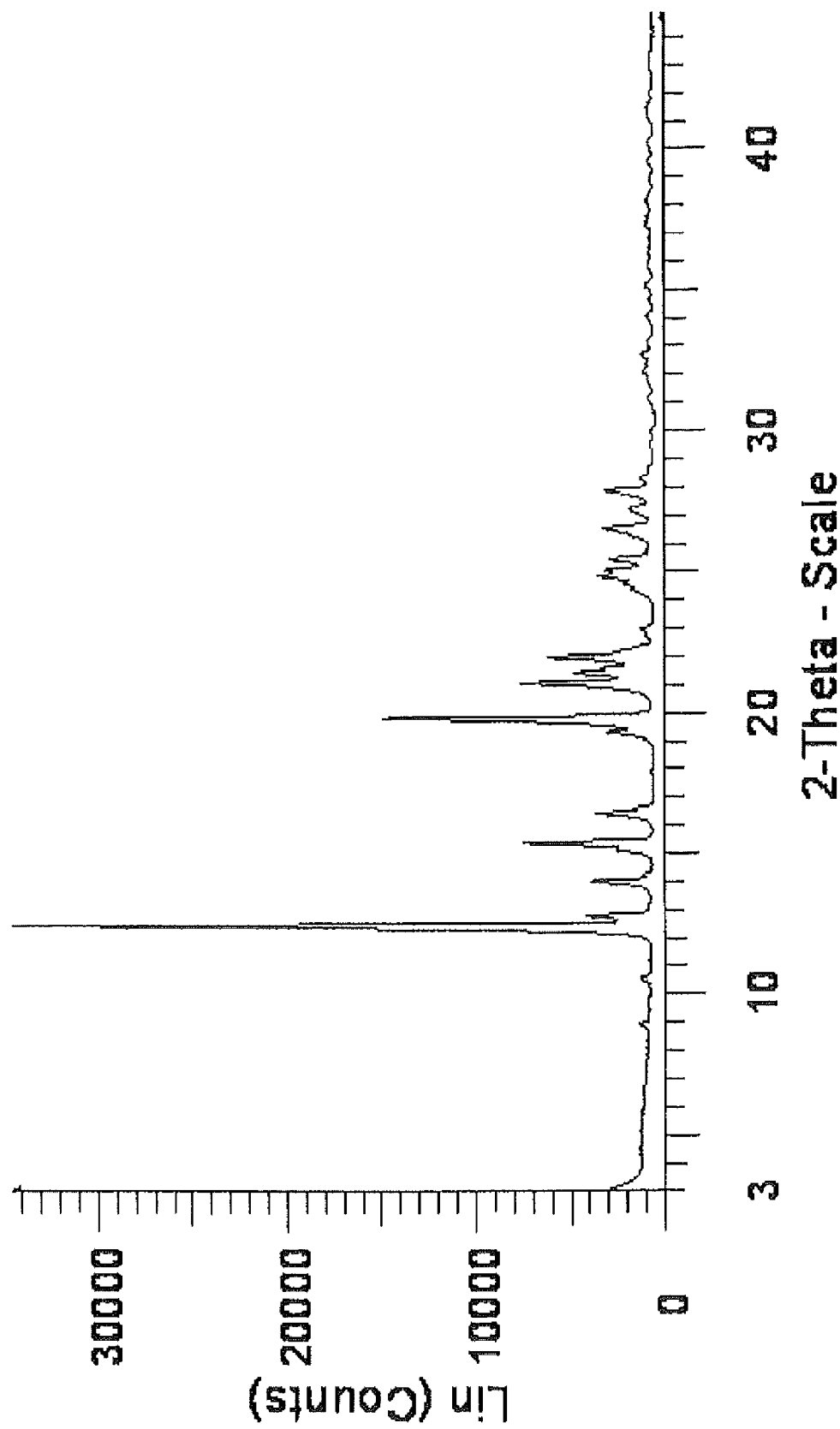
FIG. 11 is a characteristic Powder X-ray Diffraction (XRD) pattern of solid state form of tapentadol salicylate salt.
Figure 12:
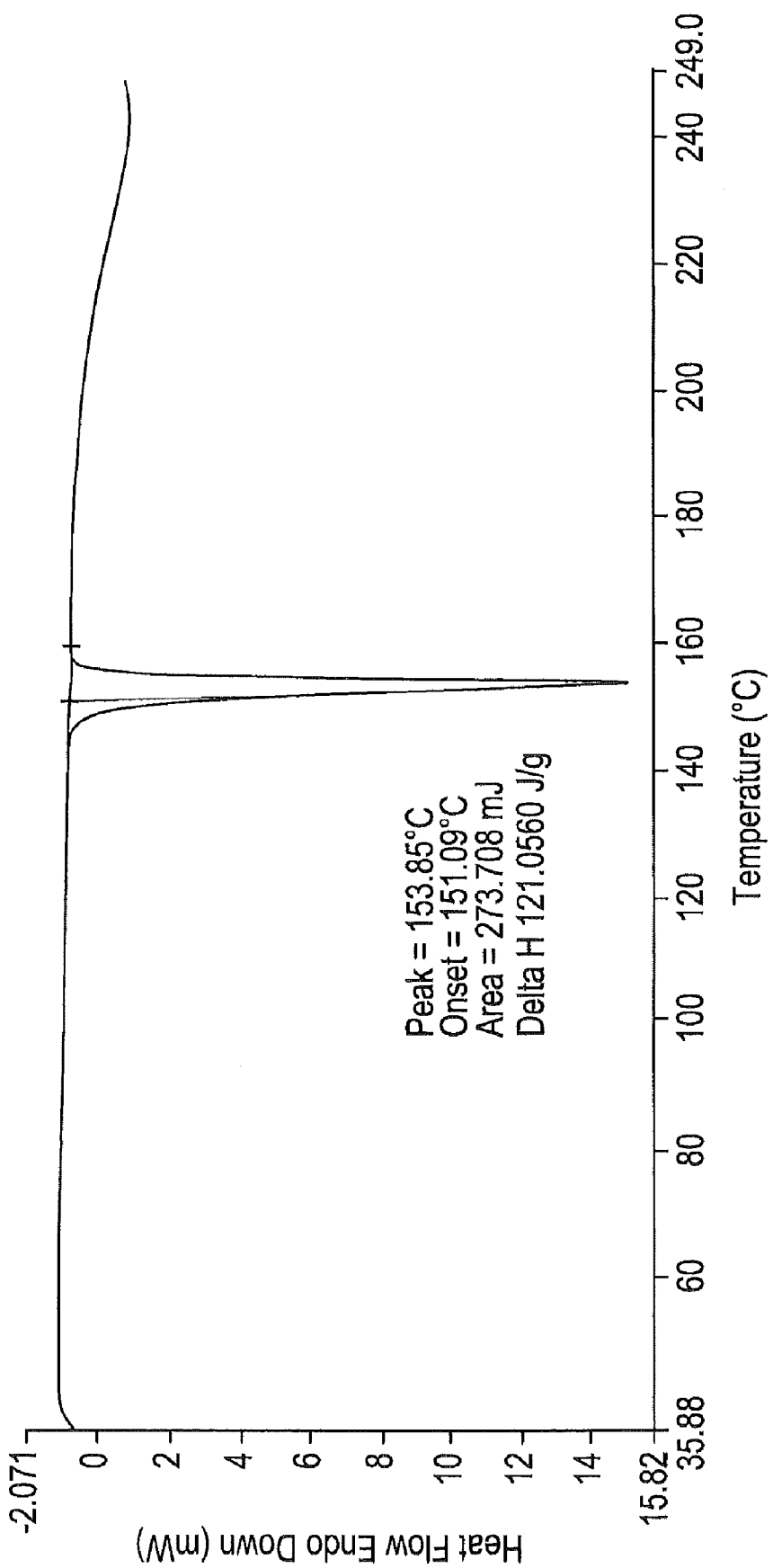
FIG. 12 is a characteristic Differential Scanning Calorimetric (DSC) thermogram of solid state form of tapentadol salicylate salt.

In one embodiment, the solid state forms of tapentadol salts have the following characteristics, wherein:

a) the solid state form of tapentadol L-(−)-camphorsulfonate salt is characterized by one or more of the following properties:
   i) a powder X-ray diffraction pattern substantially in accordance with FIG. 1;
   ii) a powder X-ray diffraction pattern having peaks at about 3.93, 5.66, 14.94, 16.16 and 21.52±0.2 degrees 2-theta;
   iii) a powder X-ray diffraction pattern having additional peaks at about 8.01, 11.36, 14.10, 15.27, 15.91, 16.72, 19.06, 19.88, 21.85, 22.56, 23.92 and 27.12±0.2 degrees 2-theta; and
   iv) a differential scanning calorimetric (DSC) thermogram substantially in accordance with FIG. 2;

b) the solid state form of tapentadol dibenzoyl-(L)-tartrate salt is characterized by one or more of the following properties:

i) a powder X-ray diffraction pattern substantially in accordance with FIG. 3;
ii) a powder X-ray diffraction pattern having peaks at about 4.83, 5.76, 9.61, 16.08, 17.40 and 17.82±0.2 degrees 2-theta;
iii) a powder X-ray diffraction pattern having additional peaks at about 11.72, 13.26, 14.39, 17.19, 18.14, 18.90, 19.19, 20.88, 21.53, 21.88, 22.43, 22.78, 23.31, 23.53, 24.06, 26.58, 27.26, 27.98, 31.22, 34.75 and 34.96±0.2 degrees 2-theta; and
iv) a differential scanning calorimetric (DSC) thermogram substantially in accordance with FIG. 4;
c) the solid state form of tapentadol dibenzoyl-(D)-tartrate salt is characterized by one or more of the following properties:
i) a powder X-ray diffraction pattern substantially in accordance with FIG. 5;
ii) a powder X-ray diffraction pattern having peaks at about 8.52, 9.39, 11.81, 12.28, 13.46, 14.06, 17.77, 17.97, 18.33, 18.79, 19.58 and 20.05±0.2 degrees 2-theta;
iii) a powder X-ray diffraction pattern having additional peaks at about 10.69, 11.61, 14.76, 21.41, 21.66, 22.19, 22.96, 23.23, 24.38, 25.72, 26.42, 27.60, 27.82, 28.29, 28.46 and 30.65±0.2 degrees 2-theta; and
iv) a differential scanning calorimetric (DSC) thermogram substantially in accordance with FIG. 6;
d) the solid state form of tapentadol malate salt is characterized by one or more of the following properties:
i) a powder X-ray diffraction pattern substantially in accordance with FIG. 7;
ii) a powder X-ray diffraction pattern having peaks at about 9.80, 19.74, 20.27, 22.87 and 24.85±0.2 degrees 2-theta;
iii) a powder X-ray diffraction pattern having additional peaks at about 17.63, 22.56, 26.30, 26.74, 30.67, 31.15, 33.73, 34.12, 35.89, 38.19, 39.27, 41.27 and 43.44±0.2 degrees 2-theta; and
iv) a differential scanning calorimetric (DSC) thermogram substantially in accordance with FIG. 8;
e) the solid state form of tapentadol maleate salt is characterized by one or more of the following properties:
i) a powder X-ray diffraction pattern substantially in accordance with FIG. 9;
ii) a powder X-ray diffraction pattern having peaks at about 15.31, 16.08, 21.08, 27.95, 28.53 and 29.51±0.2 degrees 2-theta;
iii) a powder X-ray diffraction pattern having peaks at about 19.13, 20.44, 22.90, 24.76, 30.66, 31.06, 31.81, 33.80, 34.84, 35.29, 38.31, 40.26, 40.68 and 43.16±0.2 degrees 2-theta; and
iv) a differential scanning calorimetric (DSC) thermogram substantially in accordance with FIG. 10;
f) the solid state form of tapentadol salicylate salt is characterized by one or more of the following properties:
i) a powder X-ray diffraction pattern substantially in accordance with FIG. 11;
ii) a powder X-ray diffraction pattern having peak at about 12.42, 12.75, 13.98, 15.37 and 19.81±0.2 degrees 2-theta;
iii) a powder X-ray diffraction pattern having peak at about 16.39, 19.31, 21.06, 21.41, 21.98, 24.85, 25.03, 25.45, 26.54 and 27.88±0.2 degrees 2-theta; and
iv) a differential scanning calorimetric (DSC) thermogram substantially in accordance with FIG. 12.

The solid state forms of tapentadol salts are stable, consistently reproducible, and are particularly suitable for bulk preparation and handling. Moreover, the solid state forms of tapentadol salts are useful intermediates in the preparation of tapentadol free base and its hydrochloride salt in high purity. Specifically, the preparation of solid state form of tapentadol dibenzoyl-(D)-tartrate salt is advantageous since the product can be resolved and purified by removing undesired isomers at final stage, thereby producing tapentadol or a pharmaceutically acceptable salt thereof in high enantiomeric and chemical purity.

According to another aspect, there is provided a process for the preparation of a solid state form of a tapentadol salt, wherein the salt of tapentadol is an L-(−)-camphorsulfonate salt, a dibenzoyl-(L)-tartrate salt, a dibenzoyl-(D)-tartrate salt, a malate salt, a maleate salt or a salicylate salt, comprising:

a) providing a first solution or a suspension of tapentadol free base in a solvent, wherein the solvent is water, an alcohol, a ketone, a nitrile, a polar aprotic solvent, or a mixture thereof;

b) combining the first solution or suspension with an acid to produce a second solution or suspension containing a tapentadol acid addition salt, wherein the acid is selected from the group consisting of L-(−)-camphorsulfonic acid, dibenzoyl-(L)-tartaric acid, dibenzoyl-(D)-tartaric acid, malic acid, maleic acid and salicylic acid; and c) isolating and/or recovering the solid state form of the tapentadol salt from the second solution or suspension obtained in step-(b).

The process can produce the solid state forms of tapentadol salts in substantially pure form.

The term "substantially pure solid state form of tapentadol salt" refers to the solid state form of tapentadol salt having a purity of greater than about 98 wt %, specifically greater than about 99 wt %, more specifically greater than about 99.5 wt %, and still more specifically greater than about 99.9 wt %. The purity is preferably measured by High Performance Liquid Chromatography (HPLC). For example, the purity of the solid state form of tapentadol salt obtained by the process disclosed herein can be about 98% to about 99.95%, or about 99% to about 99.99%, as measured by HPLC.

In one embodiment, the process disclosed herein provides stable solid state forms of tapentadol salts. The term "stable solid state form" refers to stability of the solid state form under the standard temperature and humidity conditions of testing of pharmaceutical products, wherein the stability is indicated by preservation of the original solid state form.

In another embodiment, the solid state forms of tapentadol salts disclosed herein remain in the same solid state form and are stable, when stored at a temperature of about 25±2° C. and at a relative humidity of about 55±5% for a period of at least one month.

In still another embodiment, the solid state forms of tapentadol salts disclosed herein remain in the same solid state form and are stable, when stored at a temperature of about 25±2° C. and at a relative humidity of about 55±5% for a period of 3 months.

The term "remains stable", as defined herein, refers to lack of formation of impurities, while being stored as described hereinbefore.

In one embodiment, the solvent used in step-(a) is selected from the group consisting of water, methanol, ethanol, n-propanol, isopropyl alcohol, isobutanol, n-butanol, tert-butanol, amyl alcohol, isoamyl alcohol, hexanol, acetone, methyl ethyl ketone, methyl isobutyl ketone, methyl tert-butyl ketone, acetonitrile, N,N-dimethylformamide, N,N-dimethylacetamide, dimethylsulfoxide, and mixtures thereof.

Specifically, the solvent is selected from the group consisting of water, methanol, ethanol, isopropyl alcohol, acetone, acetonitrile, and mixtures thereof; and more specifically water, methanol, ethanol, isopropyl alcohol, acetonitrile, and mixtures thereof.

Step-(a) of providing a first solution of tapentadol free base includes dissolving tapentadol free base in the solvent, or obtaining an existing solution from a previous processing step.

In one embodiment, the tapentadol is dissolved in the solvent at a temperature of below about the boiling temperature of the solvent used, specifically at about 20° C. to about 110° C., and more specifically at about 25° C. to about 80° C.

In another embodiment, step-(a) of providing a suspension of tapentadol free base includes suspending tapentadol free base in the solvent while stirring at a temperature of about 0° C. to the reflux temperature of the solvent used. In one embodiment, the suspension is stirred at a temperature of about 20° C. to about 110° C. for at least 30 minutes, and more specifically at a temperature of about 25° C. to about 80° C. for about 1 hour to about 10 hours.

The first solution or suspension obtained in step-(a) is optionally stirred at a temperature of about 25° C. to the reflux temperature of the solvent used for at least 15 minutes, and specifically at a temperature of about 40° C. to the reflux temperature of the solvent used for about 20 minutes to about 5 hours.

As used herein, "reflux temperature" means the temperature at which the solvent or solvent system refluxes or boils at atmospheric pressure.

The acid in step-(b) may be used directly or in the form of a solution containing the acid and a solvent. The solvent used for dissolving the acid is selected from the group as described above.

Combining of the first solution or suspension with acid in step-(b) is done in a suitable order, for example, the first solution or suspension is added to the acid, or alternatively, the acid is added to the first solution or suspension. The addition is, for example, carried out drop wise or in one portion or in more than one portion. The addition is specifically carried out at a temperature of below about 50° C., more specifically at about 15° C. to about 35° C., and most specifically at about 20° C. to about 30° C. under stirring. After completion of the addition process, the resulting mass is heated and stirred at a temperature of about 50° C. to the reflux temperature of the solvent used for at least 10 minutes, specifically at about 55° C. to about 100° C. for about 20 minutes to about 10 hours, and more specifically at a temperature of about 60° C. to about 90° C. for about 30 minutes to about 4 hours to produce a second solution or suspension.

The second solution obtained in step-(b) is optionally subjected to carbon treatment or silica gel treatment. The carbon treatment or silica gel treatment is carried out by methods known in the art, for example, by stirring the solution with finely powdered carbon or silica gel at a temperature of below about 70° C. for at least 15 minutes, specifically at a temperature of about 40° C. to about 70° C. for at least 30 minutes; and filtering the resulting mixture through hyflo to obtain a filtrate containing tapentadol acid addition salt by removing charcoal or silica gel. Specifically, the finely powdered carbon is an active carbon. A specific mesh size of silica gel is 40-500 mesh, and more specifically 60-120 mesh.

The isolation of pure solid state form of tapentadol salt in step-(c) is carried out by crystallization, substantial removal of the solvent from the solution or suspension, or a combination thereof.

Crystallization may be initiated by a method usually known in the art such as cooling, seeding, partial removal of the solvent from the solution, by adding an anti-solvent to the solution or a combination thereof.

The term "anti-solvent" refers to a solvent which when added to an existing solution of a substance reduces the solubility of the substance.

Exemplary anti-solvents include, but are not limited to, a hydrocarbon, an ether, and mixtures thereof. Specifically, the anti-solvent is selected from the group consisting of n-pentane, n-hexane, n-heptane, cyclohexane, toluene, xylene, tetrahydrofuran, dioxane, diethyl ether, diisopropyl ether, monoglyme, diglyme, and mixtures thereof; and most specifically diethyl ether, diisopropyl ether, and mixtures thereof.

In one embodiment, the crystallization is carried out by cooling the solution while stirring at a temperature of below 30° C. for at least 10 minutes, specifically at about 0° C. to about 25° C. for about 30 minutes to about 20 hours.

The term "substantially removing" the solvent refers to at least 80%, specifically greater than about 85%, more specifically greater than about 90%, still more specifically greater than about 99%, and most specifically essentially complete (100%), removal of the solvent from the second solution or suspension.

Removal of solvent is accomplished, for example, by substantially complete evaporation of the solvent, concentrating the solution or distillation of solvent, under inert atmosphere to obtain solid state form of tapentadol salt.

In one embodiment, the solvent is removed by evaporation. Evaporation can be achieved at sub-zero temperatures by lyophilisation or freeze-drying techniques. The solution may also be completely evaporated in, for example, a pilot plant Rota vapor, a Vacuum Paddle Dryer or in a conventional reactor under vacuum above about 720 mm Hg by flash evaporation techniques by using an agitated thin film dryer ("ATFD"), or evaporated by spray drying to obtain a dry amorphous powder.

The distillation process can be performed at atmospheric pressure or reduced pressure. Specifically, the solvent is removed at a pressure of about 760 mm Hg or less, more specifically at about 400 mm Hg or less, still more specifically at about 80 mm Hg or less, and most specifically from about 30 to about 80 mm Hg.

Solvents can also be removed by spray-drying, in which a solution of tapentadol salt is sprayed into the spray drier at the flow rate of 10 to 300 ml/hr, specifically 40 to 200 ml/hr. The air inlet temperature to the spray drier used is about 30° C. to about 150° C., specifically about 65° C. to about 110° C. and the outlet air temperature used is about 30° C. to about 90° C.

Another suitable method is vertical agitated thin-film drying (or evaporation). Agitated thin film evaporation technology involves separating the volatile component using indirect heat transfer coupled with mechanical agitation of the flowing film under controlled conditions. In vertical agitated thin-film drying (or evaporation) (ATFD-V), the starting solution is fed from the top into a cylindrical space between a centered rotary agitator and an outside heating jacket. The rotor rotation agitates the downside-flowing solution while the heating jacket heats it.

The recovery in step-(c) is carried out by methods such as filtration, filtration under vacuum, decantation, centrifugation, or a combination thereof. In one embodiment, the solid state form of tapentadol salt is recovered by filtration employing a filtration media of, for example, a silica gel or celite.

The substantially pure solid state form of tapentadol salt obtained by above process may be further dried in, for example, a Vacuum tray dryer, a Rotocon vacuum dryer, a Vacuum paddle dryer or a pilot plant Rota vapor, to further lower residual solvents. Drying can be carried out under reduced pressure until the residual solvent content reduces to the desired amount such as an amount within the limits given by the International Conference on Harmonization of Technical Requirements for Registration of Pharmaceuticals for human use (ICH) guide lines.

In one embodiment the drying is carried out at atmospheric pressure or reduced pressures, such as below about 200 mm Hg, or below about 50 mm Hg, at temperatures such as 35° C. to about 80° C. The drying can be carried out for any desired time period that achieves the desired result, such as about 1 to 20 hours. Drying may also be carried out for shorter or longer periods of time depending on the product specifications. Temperature and pressure are chosen based on the volatility of the solvent being used and the foregoing should be considered as only a general guidance. Dying can be suitably carried out in a tray dryer, a vacuum oven, an air oven, or using a fluidized bed drier, a spin flash dyer, a flash dryer and the like. Drying equipment selection is well within the ordinary skill in the art.

The solid state form of tapentadol salt obtained by the process disclosed herein is further optionally converted into tapentadol free base or its hydrochloride salt by treating the solid state form of tapentadol salt with a base and/or hydrochloric acid.

The treatment of the solid state form of tapentadol salt with a base and/or an hydrochloric acid is carried out in a solvent selected from the group consisting of water, methanol, ethanol, n-propanol, isopropanol, n-butanol, isobutanol, tert-butanol, amyl alcohol, hexanol, acetone, methyl ethyl ketone, methyl isobutyl ketone, methyl tert-butyl ketone, acetonitrile, ethyl acetate, methyl acetate, isopropyl acetate, tert-butyl methyl acetate, ethyl formate, dichloromethane, dichloroethane, chloroform, carbon tetrachloride, tetrahydrofuran, dioxane, diethyl ether, diisopropyl ether, monoglyme, diglyme, n-pentane, n-hexane, n-heptane, cyclohexane, toluene, xylene, N,N-dimethylformamide, N,N-dimethylacetamide, dimethylsulfoxide, and mixtures thereof.

The base suitable for converting the solid state form of tapentadol salt into tapentadol free base or a pharmaceutically acceptable salt thereof is an organic or inorganic base. Specific organic bases are triethyl amine, trimethylamine, N,N-diisopropylethylamine, N-methylmorpholine and N-methylpiperidine.

In another embodiment, the base is an inorganic base. Exemplary inorganic bases include, but are not limited to, ammonia; hydroxides, alkoxides, carbonates and bicarbonates of alkali or alkaline earth metals. Specific inorganic bases are ammonia, sodium hydroxide, calcium hydroxide, magnesium hydroxide, potassium hydroxide, lithium hydroxide, sodium carbonate, potassium carbonate, lithium carbonate, sodium tert-butoxide, sodium isopropoxide and potassium tert-butoxide, and more specifically ammonia, sodium hydroxide, potassium hydroxide, sodium carbonate and potassium carbonate.

The hydrochloric acid used may be in the form of concentrated hydrochloric acid, aqueous hydrochloric acid, in the form of hydrogen chloride gas, or hydrogen chloride dissolved in an organic solvent. The organic solvent used for dissolving hydrogen chloride gas or hydrogen chloride is selected from the group consisting of ethanol, methanol, isopropyl alcohol, ethyl acetate, diethyl ether, dimethyl ether, acetone, and mixtures thereof.

Further encompassed herein is the use of the solid state form of a tapentadol salt for the manufacture of a pharmaceutical composition together with a pharmaceutically acceptable carrier, wherein the salt of tapentadol is an L-(−)-camphorsulfonate salt, a dibenzoyl-(L)-tartrate salt, a dibenzoyl-(D)-tartrate salt, a malate salt, a maleate salt or a salicylate salt.

A specific pharmaceutical composition of the solid state form of tapentadol salt is selected from a solid dosage form and an oral suspension.

In one embodiment, the solid state form of tapentadol salt has a $D_{90}$ particle size of less than or equal to about 500 microns, specifically about 1 micron to about 300 microns, and most specifically about 10 microns to about 150 microns, wherein the salt of tapentadol is an L-(−)-camphorsulfonate salt, a dibenzoyl-(L)-tartrate salt, a dibenzoyl-(D)-tartrate salt, a malate salt, a maleate salt or a salicylate salt.

In another embodiment, the particle sizes of the solid state form of tapentadol salt are produced by a mechanical process of reducing the size of particles which includes any one or more of cutting, chipping, crushing, milling, grinding, micronizing, trituration or other particle size reduction methods known in the art, to bring the solid state form to the desired particle size range.

According to another aspect, there is provided pharmaceutical compositions comprising the solid state form of tapentadol salt and one or more pharmaceutically acceptable excipients, wherein the salt of tapentadol is an L-(−)-camphorsulfonate salt, a dibenzoyl-(L)-tartrate salt, a dibenzoyl-(D)-tartrate salt, a malate salt, a maleate salt or a salicylate salt.

According to another aspect, there is provided pharmaceutical compositions comprising the solid state form of tapentadol salt prepared according to process disclosed herein and one or more pharmaceutically acceptable excipients, wherein the salt of tapentadol is an L-(−)-camphorsulfonate salt, a dibenzoyl-(L)-tartrate salt, a dibenzoyl-(D)-tartrate salt, a malate salt, a maleate salt or a salicylate salt.

According to another aspect, there is provided a process for preparing a pharmaceutical formulation comprising combining the solid state form of tapentadol salt prepared according to processes disclosed herein, with one or more pharmaceutically acceptable excipients, wherein the salt of tapentadol is an L-(−)-camphorsulfonate salt, a dibenzoyl-(L)-tartrate salt, a dibenzoyl-(D)-tartrate salt, a malate salt, a maleate salt or a salicylate salt.

According to another aspect, there is provided a method for treating a patient suffering from severe acute pain; comprising administering a solid state form of tapentadol salt, or a pharmaceutical composition that comprises the solid state form of tapentadol salt along with pharmaceutically acceptable excipients, wherein the salt of tapentadol is an L-(−)-camphorsulfonate salt, a dibenzoyl-(L)-tartrate salt, a dibenzoyl-(D)-tartrate salt, a malate salt, a maleate salt or a salicylate salt.

Yet in another embodiment, pharmaceutical compositions comprise at least a therapeutically effective amount of solid state form of a tapentadol salt, wherein the salt of tapentadol is an L-(−)-camphorsulfonate salt, a dibenzoyl-(L)-tartrate salt, a dibenzoyl-(D)-tartrate salt, a malate salt, a maleate salt or a salicylate salt. Such pharmaceutical compositions may be administered to a mammalian patient in a dosage form, e.g., solid, liquid, powder, elixir, aerosol, syrups, injectable solution, etc. Dosage forms may be adapted for administration to the patient by oral, buccal, parenteral, ophthalmic, rectal and transdermal routes or any other acceptable route of administration. Oral dosage forms include, but are not limited to, tablets, pills, capsules, syrup, troches, sachets, suspensions, powders, lozenges, elixirs and the like. The solid state form of tapentadol salt may also be administered as suppositories, ophthalmic ointments and suspensions, and parenteral suspensions, which are administered by other routes, wherein the salt of tapentadol is an L-(−)-camphorsulfonate salt, a dibenzoyl-(L)-tartrate salt, a dibenzoyl-(D)-tartrate salt, a malate salt, a maleate salt or a salicylate salt.

The pharmaceutical compositions further contain one or more pharmaceutically acceptable excipients. Suitable excipients and the amounts to use may be readily determined by the formulation scientist based upon experience and consideration of standard procedures and reference works in the field, e.g., the buffering agents, sweetening agents, binders, diluents, fillers, lubricants, wetting agents and disintegrants described herein.

In one embodiment, capsule dosage forms contain solid state form of tapentadol salt within a capsule which may be coated with gelatin. Tablets and powders may also be coated with an enteric coating. Suitable enteric coating include phthalic acid cellulose acetate, hydroxypropylmethyl cellulose phthalate, polyvinyl alcohol phthalate, carboxy methyl ethyl cellulose, a copolymer of styrene and maleic acid, a copolymer of methacrylic acid and methyl methacrylate, and like materials, and if desired, the coating agents may be employed with suitable plasticizers and/or extending agents. A coated capsule or tablet may have a coating on the surface thereof or may be a capsule or tablet comprising a powder or granules with an enteric-coating.

Tableting compositions may have few or many components depending upon the tableting method used, the release rate desired and other factors. For example, the compositions described herein may contain diluents such as cellulose-derived materials such as powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents such as calcium carbonate and calcium diphosphate and other diluents known to one of ordinary skill in the art. Yet other suitable diluents include waxes, sugars (e.g. lactose) and sugar alcohols such as mannitol and sorbitol, acrylate polymers and copolymers, as well as pectin, dextrin and gelatin.

Other excipients include binders, such as acacia gum, pregelatinized starch, sodium alginate, glucose and other binders used in wet and dry granulation and direct compression tableting processes; disintegrants such as sodium starch glycolate, crospovidone, low-substituted hydroxypropyl cellulose and others; lubricants like magnesium and calcium stearate and sodium stearyl fumarate; flavorings; sweeteners; preservatives; pharmaceutically acceptable dyes and glidants such as silicon dioxide.

Instrumental Details:
High Pressure Liquid Chromatography:
The HPLC purity was measured by high performance liquid chromatography by using Waters, alliance 2695 HPLC system having dual wavelength and 2487 UV detector under the following conditions:
Column: ACE-3-C18, 150*4.6 mm, Part Number-ACE-111-1546.
Column oven temperature: 25° C.
Detection: UV at 237 nm and 210 nm
Flow rate: 1.0 mL/minute
Injection volume: 10 µL
Run time: 55 minutes
Diluents: Water:acetonitrile (50:50 v/v)
Sample concentration: Prepare a mixture of 2.0 mg/ml of sample in diluents.
X-Ray Powder Diffraction (P-XRD):

The X-Ray powder diffraction was measured by an X-ray powder diffractometer equipped with CuKα-radiations (40 kV, 40 mA) in wide-angle X-ray diffractometer of BRUKER axs, D8 ADVANCE. The sample was analyzed using the following instrument parameters: measuring range=3-45° 2-theta; step width=0.01579°; and measuring time per step=0.11 sec.
Differential Scanning Calorimetry (DSC):
Differential Scanning Calorimetry (DSC) measurements were performed with a Differential Scanning Calorimeter (DSC Q 1000 V23.5 Build 72, Universal V4.3A TA Instruments) at a scan rate of 5° C. per minute.

REFERENCE EXAMPLE

Preparation of Tapentadol Hydrochloride Salt as Per the Process Disclosed in U.S. Pat. No. 6,248,737

Tapentadol free base (2.1 g) was added to 2-butanone (32 ml), the mixture was heated to reflux and followed by the addition of water (0.22 ml) and trimethylchlorosilane (1.6 ml) at the same temperature and then maintaining for 1 hour. The resulting mass was cooled at 20-25° C. The resulting solid was filtered, the product was washed with pre-cooled 2-butanone (4 ml) and then the solid was dried at 25° C. for 3 hours to produce 1.8 g of tapentadol hydrochloride salt (Purity by HPLC: 97.78%).

The following examples are given for the purpose of illustrating the present disclosure and should not be considered as limitation on the scope or spirit of the disclosure.

EXAMPLES

Example 1

Preparation of Solid State Form of Tapentadol L-(−)-Camphorsulfonate Salt

Tapentadol (2 g) was dissolved in isopropyl alcohol (20 ml), followed by the addition of (L)-camphorsulfonic acid (2.5 g) to the solution at 25-30° C. and heating the reaction mass at 70-75° C. The resulting solution was slowly cooled to 20-25° C. and stirred for 2 hours at 20-25° C. The resulting solid was filtered, washed with isopropyl alcohol (5 ml) and dried at 40-45° C. under vacuum to give 0.6 g of tapentadol L-(−)-camphorsulfonate salt.

Example 2

Preparation of Solid State Form of Tapentadol Dibenzoyl-(L)-Tartrate Salt

Tapentadol (2 g) was dissolved in isopropyl alcohol (20 ml), followed by the addition of dibenzoyl-(L)-tartaric acid (4 g) to the solution at 25-30° C. and heating the reaction mass at 80-85° C. The resulting solution was slowly cooled to 20-25° C. and stirred for 2 hours at 20-25° C. The resulting solid was collected by filtration, washed with isopropyl alcohol (5 ml) and dried at 40-45° C. under vacuum to give 1.2 g of tapentadol dibenzoyl-(L)-tartrate salt (Purity by HPLC: 99.7%).

Example 3

Preparation of Solid State Form of Tapentadol Dibenzoyl-(D)-Tartrate Salt

Isopropyl alcohol (25 ml) was added to dibenzoyl-(D)-tartaric acid (7 g), the mixture was stirred for 20 minutes and followed by the addition of a solution of tapentadol free base (4 g) in isopropyl alcohol (15 ml) at 25-30° C. The resulting solution was stirred for 15 minutes, followed by heating at 80° C. and then stiffing for 15 minutes. The resulting mass was slowly cooled to 20-25° C. and stirred for 12 hours. The resulting solid was filtered, washed with isopropyl alcohol (4 ml) and then the solid was dried at 40° C. under vacuum for 6 hours to produce 7.3 g of tapentadol dibenzoyl-(D)-tartrate salt (Purity by HPLC: 99.68%).

Example 4

Preparation of Solid State Form of Tapentadol (DL)-Malate Salt

Tapentadol (2 g) was dissolved in isopropyl alcohol (15 ml), followed by the addition of (dl)-malic acid (1.45 g) to the solution at 25-30° C. and heating the reaction mass at 80-85° C. The resulting solution was slowly cooled to 20-25° C. and stirred for 2 hours at 20-25° C. The resulting solid was collected by filtration, washed with isopropyl alcohol (5 ml) and dried at 40-45° C. under vacuum to give 0.8 g of tapentadol (DL)-malate salt.

Example 5

Preparation of Solid State Form of Tapentadol Maleate Salt

Tapentadol (2 g) was dissolved in acetonitrile (15 ml), followed by addition of maleic acid (1.25 g) to the solution at 25-30° C. and heating the reaction mass at 80-85° C. The resulting solution was slowly cooled to 20-25° C. and stirred for 2 hours at 20-25° C. The resulting solid was collected by filtration, washed with acetonitrile (5 ml) and dried at 40-45° C. under vacuum to give 0.5 g of tapentadol maleate salt.

Example 6

Preparation of Solid State Form of Tapentadol Salicylate Salt

Tapentadol (2 g) was dissolved in acetonitrile (15 ml), followed by addition of salicylic acid (1.25 g) to the solution at 25-30° C. and heating the reaction mass at 80-85° C. The resulting solution was slowly cooled to 20-25° C. and stirred for 2 hours at 20-25° C. The resulting solid was collected by filtration, washed with acetonitrile (10 ml) and dried at 40-45° C. under vacuum to give 2.5 g of tapentadol salicylate salt (Purity by HPLC: 99.75%).

Unless otherwise indicated, the following definitions are set forth to illustrate and define the meaning and scope of the various terms used to describe the invention herein.

The term "solid state form of tapentadol salts disclosed herein" includes crystalline forms, amorphous form, hydrated, and solvated forms of tapentadol salts.

The term "crystalline form" refers to a crystal modification that can be characterized by analytical methods such as X-ray powder diffraction, IR-spectroscopy, differential scanning calorimetry (DSC) or by its melting point.

The term "pharmaceutically acceptable" means that which is useful in preparing a pharmaceutical composition that is generally non-toxic and is not biologically undesirable, and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

The term "therapeutically effective amount" as used herein means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The term "delivering" as used herein means providing a therapeutically effective amount of an active ingredient to a particular location within a host causing a therapeutically effective blood concentration of the active ingredient at the particular location. This can be accomplished, e.g., by topical, local or by systemic administration of the active ingredient to the host.

The term "buffering agent" as used herein is intended to mean a compound used to resist a change in pH upon dilution or addition of acid of alkali. Such compounds include, by way of example and without limitation, potassium metaphosphate, potassium phosphate, monobasic sodium acetate and sodium citrate anhydrous and dihydrate and other such material known to those of ordinary skill in the art.

The term "sweetening agent" as used herein is intended to mean a compound used to impart sweetness to a formulation. Such compounds include, by way of example and without limitation, aspartame, dextrose, glycerin, mannitol, saccharin sodium, sorbitol, sucrose, fructose and other such materials known to those of ordinary skill in the art.

The term "binders" as used herein is intended to mean substances used to cause adhesion of powder particles in granulations. Such compounds include, by way of example and without limitation, acacia, alginic acid, tragacanth, carboxymethylcellulose sodium, polyvinylpyrrolidone, compressible sugar (e.g., NuTab), ethylcellulose, gelatin, liquid glucose, methylcellulose, pregelatinized starch, starch, polyethylene glycol, guar gum, polysaccharide, bentonites, sugars, invert sugars, poloxamers (PLURONIC™ F68, PLURONIC™ F127), collagen, albumin, celluloses in non-aqueous solvents, polypropylene glycol, polyoxyethylene-polypropylene copolymer, polyethylene ester, polyethylene sorbitan ester, polyethylene oxide, microcrystalline cellulose, combinations thereof and other material known to those of ordinary skill in the art.

The term "diluent" or "filler" as used herein is intended to mean inert substances used as fillers to create the desired bulk, flow properties, and compression characteristics in the preparation of solid dosage formulations. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

The term "glidant" as used herein is intended to mean agents used in solid dosage formulations to improve flow-properties during tablet compression and to produce an anti-caking effect. Such compounds include, by way of example and without limitation, colloidal silica, calcium silicate, magnesium silicate, silicon hydrogel, cornstarch, talc, combinations thereof and other such materials known to those of ordinary skill in the art.

The term "lubricant" as used herein is intended to mean substances used in solid dosage formulations to reduce friction during compression of the solid dosage. Such compounds include, by way of example and without limitation, calcium stearate, magnesium stearate, mineral oil, stearic acid, zinc stearate, combinations thereof and other such materials known to those of ordinary skill in the art.

The term "disintegrant" as used herein is intended to mean a compound used in solid dosage formulations to promote the disruption of the solid mass into smaller particles which are more readily dispersed or dissolved. Exemplary disintegrants include, by way of example and without limitation, starches such as corn starch, potato starch, pregelatinized, sweeteners, clays, such as bentonite, microcrystalline cellulose (e.g., Avicel™), carsium (e.g., Amberlite™), alginates, sodium starch glycolate, gums such as agar, guar, locust bean, karaya, pectin, tragacanth, combinations thereof and other such materials known to those of ordinary skill in the art.

The term "wetting agent" as used herein is intended to mean a compound used to aid in attaining intimate contact between solid particles and liquids. Exemplary wetting agents include, by way of example and without limitation, gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters, (e.g., TWEEN™s), polyethylene glycols, polyoxyethylene stearates colloidal silicon dioxide, phosphates, sodium dodecylsulfate, carboxymethylcellulose calcium, carboxymethylcellulose sodium, methylcellulose, hydroxyethylcellulose, hydroxylpropylcellulose, hydroxypropylmethylcellulose phthalate, noncrystalline cellulose, magnesium aluminum silicate, triethanolamine, polyvinyl alcohol, and polyvinylpyrrolidone (PVP). Tyloxapol (a nonionic liquid polymer of the alkyl aryl polyether alcohol type) is another useful wetting agent, combinations thereof and other such materials known to those of ordinary skill in the art.

The term "micronization" used herein means a process or method by which the size of a population of particles is reduced.

As used herein, the term "micron" or "μm" both are same refers to "micrometer" which is $1\times10^{-6}$ meter.

As used herein, "crystalline particles" means any combination of single crystals, aggregates and agglomerates.

As used herein, "Particle Size Distribution (P.S.D)" means the cumulative volume size distribution of equivalent spherical diameters as determined by laser diffraction in Malvern Master Sizer 2000 equipment or its equivalent.

The important characteristics of the PSD are the ($D_{90}$), which is the size, in microns, below which 90% of the particles by volume are found, and the ($D_{50}$), which is the size, in microns, below which 50% of the particles by volume are found. Thus, a $D_{90}$ or d(0.9) of less than 300 microns means that 90 volume-percent of the particles in a composition have a diameter less than 300 microns.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. Solid state form of a salt of 3-[(1R,2R)-3-(dimethylamino)-1-ethyl-2-methylpropyl] phenol (tapentadol salt), wherein the salt of tapentadol is a dibenzoyl-(L)-tartrate salt, characterized by one or more of the following properties:
   i) a powder X-ray diffraction pattern in accordance with FIG. 3;
   ii) a powder X-ray diffraction pattern having peaks at 4.83, 5.76, 9.61, 16.08, 17.40 and 17.82±0.2 degrees 2-theta;
   iii) a powder X-ray diffraction pattern having peaks at 4.83, 5.76, 9.61, 11.72, 13.26, 14.39, 16.08, 17.19, 17.40, 17.82, 18.14, 18.90, 19.19, 20.88, 21.53, 21.88, 22.43, 22.78, 23.31, 23.53, 24.06, 26.58, 27.26, 27.98, 31.22, 34.75 and 34.96±0.2 degrees 2-theta; and
   iv) a differential scanning calorimetric (DSC) thermogram in accordance with FIG. 4, wherein the dibenzoyl-(L)-tartrate salt of tapentadol is greater than 98% pure.

2. A pharmaceutical composition comprising solid state form of a tapentadol salt and one or more pharmaceutically acceptable excipients, wherein the salt of tapentadol is a dibenzoyl-(L)-tartrate salt according to claim 1.

3. The pharmaceutical composition of claim 2, wherein the pharmaceutical composition is a solid dosage form, an oral suspension, a liquid, a powder, an elixir, an aerosol, a syrup, or an injectable solution.

4. The pharmaceutical composition of claim 2, wherein the solid state form of tapentadol salt has a $D_{90}$ particle size of less than or equal to about 500 microns.

5. The pharmaceutical composition of claim 4, wherein the $D_{90}$ particle size is about 1 micron to about 300 microns, or about 10 microns to about 150 microns.

* * * * *